United States Patent
Qureshi et al.

(10) Patent No.: US 6,825,041 B2
(45) Date of Patent: Nov. 30, 2004

(54) METHOD AND SYSTEM FOR AUTOMATED IMMUNOCHEMISTRY ANALYSIS

(75) Inventors: Humayun Qureshi, Eden Prairie, MN (US); Glenn A. Davis, Minnetonka, MN (US); Mark J. Kittock, Eden Prairie, MN (US); Armer J. Willenbring, Minnetonka, MN (US); Brian D. Wilson, Chaska, MN (US); Peter G. Werness, Carver, MN (US)

(73) Assignee: Beckman Coulter, Inc., Fullerton, CA (US)

( * ) Notice: Subject to any disclaimer, the term of this patent is extended or adjusted under 35 U.S.C. 154(b) by 509 days.

(21) Appl. No.: 09/815,088

(22) Filed: Mar. 16, 2001

(65) Prior Publication Data

US 2003/0092185 A1  May 15, 2003

(51) Int. Cl.[7] .......................... G01N 35/00; G01N 35/02
(52) U.S. Cl. ............................ 436/43; 422/63; 422/64; 422/65; 422/66; 422/67; 436/47; 436/50
(58) Field of Search ............................ 422/63–67, 100; 436/180, 43, 47, 50

(56) References Cited

U.S. PATENT DOCUMENTS

| | | |
|---|---|---|
| 4,678,752 A | 7/1987 | Thorne et al. ............... 435/291 |
| 4,837,159 A * | 6/1989 | Yamada ........................ 436/45 |
| 5,055,408 A | 10/1991 | Higo et al. .................... 436/48 |
| 5,158,895 A | 10/1992 | Ashihara et al. ............. 436/526 |
| 5,380,487 A | 1/1995 | Choperena et al. ........... 422/63 |
| 5,434,083 A * | 7/1995 | Mitsumaki et al. ........... 436/48 |
| 5,482,861 A | 1/1996 | Clark et al. ................... 436/48 |
| 5,501,838 A | 3/1996 | Ootani et al. ................. 422/65 |
| 5,575,976 A | 11/1996 | Choperena et al. ........... 422/64 |
| 5,580,524 A | 12/1996 | Forrest et al. ................ 422/63 |
| 5,587,129 A | 12/1996 | Kurosaki et al. ............. 422/64 |
| 5,658,799 A | 8/1997 | Choperena et al. ........... 436/50 |
| 5,693,292 A | 12/1997 | Choperena et al. ........... 422/67 |
| 5,846,491 A | 12/1998 | Choperena et al. ........... 422/67 |
| 5,856,193 A | 1/1999 | Fanning et al. ............... 436/48 |
| 5,885,529 A | 3/1999 | Babson et al. ................ 422/65 |
| 5,885,530 A | 3/1999 | Babson et al. ................ 422/65 |

FOREIGN PATENT DOCUMENTS

| | | |
|---|---|---|
| JP | 02-025755 | 1/1990 |
| JP | 04-279862 | * 10/1992 |
| JP | 08-094629 | 4/1996 |
| WO | 93/12431 | 6/1993 |

* cited by examiner

*Primary Examiner*—Jan M. Ludlow
(74) *Attorney, Agent, or Firm*—Hogan & Hartson, LLP

(57) ABSTRACT

A method and system for automated immunochemistry or chemistry analysis are provided. The method and system provide a sample aliquoting section, a reagent pipetting section having a plurality of independent reagent pipetting stations, each operating on a cycle of a first period of time, and an incubate and wash and read section operating on a cycle of a second period of time to match the throughput of the system, where the quotient of the first period of time divided by the second period of time is a whole number, and the number of the independent reagent pipetting stations being equal to the whole number. The respective cycles of the independent reagent pipetting stations are staggered apart by the second time period, such that at least one of the multiple independent pipetting stations is available for working with the incubate and wash and read section at each operating cycle of the second period of time.

48 Claims, 3 Drawing Sheets

METHOD AND SYSTEM FOR AUTOMATED IMMUNOCHEMISTRY ANALYSIS

BACKGROUND OF THE INVENTION

1. Area of the Art

The present invention relates generally to methods and systems for automated chemical analysis, and more specifically to automated immunochemistry instruments and methodologies.

2. Description of the Prior Art

Immunochemistry instruments are widely used in clinical chemistry sampling and analyzing applications for performing various assays. The following references are found to be pertinent to the field of the present invention:

U.S. Pat. No. 4,678,752, issued to Thorne, et al. on Jul. 7, 1987, disclosed an automated apparatus for analysis of samples. The apparatus includes an introduction station and a shuttle system work with reagent packages, each containing both sample receptacles and reagent receptacles.

U.S. Pat. No. 5,055,408, issued to Higo, et al. on Oct. 8, 1991, disclosed an automated enzyme-immunoassay analyzer. The analyzer is designed to work with test plates, each having a plurality of upwardly opened immunological reaction chambers and requires a test cup storage area located below a measuring part, and ascending and descending elevators respectively associated with the upstream and downstream ends of the transfer route of the measuring part and respectively connecting the upstream and downstream ends of the transfer route with the test cup storage area for respectively circulating test plates between the transfer route and the test cup storage area.

U.S. Pat. No. 5,158,895, issued to Ashihara, et al. on Oct. 27, 1992, disclosed an automatic immunoassay apparatus. The apparatus includes a plurality of reaction cartridges, each having at least two wells, including a first well of said at least two wells containing solid phase material carrying an antigen or an antibody and a second well of said at least two wells containing an antibody or an antigen labeled with labeling compound.

U.S. Pat. No. 5,380,487, issued to Choperena, et al. on Jan. 10, 1995, disclosed a device for processing materials. The device includes a first transport means adapted to transport articles along a first treatment path and a second transport means adapted to transport articles along a second treatment path. Both transporting means are elongated movable transporting means and include indexing positions.

U.S. Pat. No. 5,482,861, issued to Clark, et al. on Jan. 9, 1996, disclosed a method of operating an automated, continuous, and random access analytical system capable of simultaneously effecting multiple assays of a plurality of liquid samples. The method includes the step of preparing at least one unit dose disposable for each sample placed onto said system by (i) transferring an aliquot of the sample to a first well located in a reaction vessel having a plurality of separate and independent wells capable of receiving liquids; (ii) transferring to a second well located in the reaction vessel at least one reagent that is necessary for affecting the scheduled assay of the sample, such that reaction between the aliquot and the at least one reagent does not occur, the step of transferring the reaction vessel containing the at least one unit dose disposable to a processing workstation, and the step of transferring at least one of the aliquot of the liquid sample or the at least one reagent in a well in the reaction vessel to a well in the reaction vessel to combine the aliquot and the at least one reagent to form a reaction mixture necessary for performing one of the scheduled assays.

U.S. Pat. No. 5,501,838, issued to Ootani, et al. on Mar. 26, 1996, disclosed an automated immunochemical analyzer. The analyzer includes a table for mounting a reaction plate, wherein the table can be drawn out, and means for judging and displaying whether it is possible or impossible to draw out the table for mounting said at least one reaction plate.

U.S. Pat. No. 5,575,976, issued to Choperena, et al. on Nov. 19, 1996, disclosed an automated chemical analyzer. The analyzer includes an incubation station comprising an elongated, movable transport means adapted to carry a plurality of reaction vessels along an incubation path, and a wash station including a movable transport means adapted to receive and carry a plurality of reaction vessels along a wash-cycle path.

U.S. Pat. No. 5,580,524, issued to Forrest, et al. on Dec. 3, 1996, disclosed an automated multi-test capability assay apparatus in modular form for nonsequential processing of samples for assay. The apparatus includes a device for ensuring solid phase suspension which includes a housing, a rotatable support having means for independently rotatably mounting a vessel around a circumference of the support, and a drive wheel for rotating the mounted vessel, where the housing includes a driving surface having longer circumferential dimensions than the drive wheel and surrounding the drive wheel and engageable therewith.

U.S. Pat. No. 5,587,129, issued to Kurosaki, et al. on Dec. 24, 1996, disclosed an apparatus for automatically analyzing a specimen. The apparatus includes a first dispensing means for dispensing specimen in a sample vial into a stock vial, a second dispensing means for dispensing the specimen in the stock vial into an assay vial, and a third dispensing means for dispensing reagent into the assay vial.

U.S. Pat. No. 5,658,799, issued to Choperena, et al. on Aug. 19, 1997, disclosed a method for automatically analyzing a plurality of samples for at least two different analytes. The method includes the step of providing a transfer control means for controlling the transfer of reaction vessels from one assay resource station to another according to a chronology selected from a plurality of predetermined different chronologies, where the chronology for determining the analyte in the first sample being a different one of the predetermined different chronologies from the chronology for determining the analyte in the second sample.

U.S. Pat. No. 5,693,292, issued to Choperena, et al on Dec. 2, 1997, disclosed an automated chemical analyzer for automatically analyzing a plurality of samples for at least two different analytes. The analyzer includes an incubation station comprising an elongated, movable transport means adapted to carry a plurality of reaction vessels along an incubation path.

U.S. Pat. No. 5,846,491, issued to Choperena, et al on Dec. 8, 1998, disclosed an automated chemical analyzer for automatically analyzing a plurality of samples for at least two different analytes. The analyzer includes a transfer control means for controlling the transfer of reaction vessels directly from one assay resource station to another, according to a chronology selected from a plurality of different predetermined chronologies.

U.S. Pat. No. 5,856,193, issued to Fanning, et al. on Jan. 5, 1999, disclosed a method for conducting identification and susceptibility testing of a biological agent in a fluid sample in an automated sample testing machine. The method includes the steps of providing a sample holder that can receive a first receptacle containing a fluid sample, an identification test sample card that is fluid communication with the fluid sample contained in the first receptacle once placed on the sample holder, a second open receptacle, and a susceptibility test sample card that is in fluid communication with the second open receptacle once placed in the sample holder.

U.S. Pat. No. 5,885,529, issued to Babson, et al. on Mar. 23, 1999, disclosed an automated immunoassay analyzer. The analyzer includes dispensing means for receiving a plurality of inert support dispensing packs.

U.S. Pat. No. 5,885,530, issued to Babson, et al. on Mar. 23, 1999, disclosed an automated immunoassay analyzer. The analyzer includes an inert support supply and dispensing means for receiving a plurality of inert support dispensing packs each storing a single type of biomaterial-coated inert support.

While various automated immunochemistry analyzers and methods have been developed, as shown in the above references, there is a need for an automated immunochemistry analyzer that is capable of having a higher throughput, and also capable of being connected to other analyzers through a common sample handling unit, and further being capable of providing multiple pipetting modules that can work independently to ensure uninterrupted analysis, even when one of the modules malfunctions. Accordingly, it is desirable to provide a new method and system for automated immunochemistry analysis that can satisfy those needs.

SUMMARY OF THE INVENTION

The present invention is directed to a new method and system for an automated immunochemistry analysis.

It is one of the primary objects of the present invention to provide a new method and system for an automated immunochemistry analysis that is capable of having a higher throughput.

It is also a primary object of the present invention to provide a new method and system for an automated immunochemistry analysis that is capable of being connected to other analyzers through a common sample handling unit.

It is another one of the primary objects of the present invention to provide a new method and system for an automated immunochemistry analysis that is capable of providing and handling multiple pipetting modules which can work independently to ensure an uninterrupted analysis, even when one of the modules malfunctions.

In addition, it is a primary object of the present invention to provide a new method and system for an automated immunochemistry analysis that is capable of performing reflex testing with a large capacity chilled sample storage area.

It is also another one of the primary objects of the present invention to provide a new method and system for an automated immunochemistry analysis that incorporates a vessel loading apparatus that is capable of handling a bulk quantity of vessels.

It is still another one of the primary objects of the present invention to provide a new method and system for an automated immunochemistry analysis that incorporates a pick-and-place transporting device, which transports the vessels among various working areas of the system without dragging or jarring the vessels or splashing the contents of the vessels.

A. Summary of the Automated Immunochemistry Analyzer of the Present Invention

Described generally, the automated immunochemistry analyzer of the present invention includes the following basic components:

1. A sample aliquoting section having an operating cycle of a first period of time, and including a main sample pipetting station for aliquoting a desired amount of a sample from a sample container to a sample vessel (SV), wherein the quotient of the first period of time divided by the third period of time described below is a whole number;
2. A chilled storage for storing multiple sample vessels containing aliquoted samples;
3. A reagent pipetting section including multiple independent pipetting stations, each having an operating cycle of a second period of time, where the quotient of the second period of time divided by the third period of time is a whole number, the number of the multiple independent pipetting stations being equal to the whole number, and the respective cycles of such stations being staggered apart by the third period of time, such that at least one of the multiple independent pipetting stations is available for accepting at least one of the sample vessels containing an aliquoted sample at each operating cycle of the sample aliquoting section;
4. A reagent storage for storing multiple reagent packs, each containing at least one reagent;
5. The multiple independent pipetting stations, each having a pipettor for aspirating a required amount of sample from the at least one of the sample vessels containing an aliquoted sample and dispensing it into an reaction vessel (RV), and aspirating a required amount of reagent from the at least one of the reagent packs containing at least one reagent and dispensing it into the reaction vessel; and
6. An incubate-wash-read section having an operating cycle of a third period of time, to match the desired throughput of the instrument system.

B. Summary of the Automated Immunochemistry Analysis of the Present Invention

Described generally, the automated immunochemistry analysis of the present invention includes the following basic steps:

1. Providing a sample aliquoting section operating on a cycle of a first period of time, where the quotient of the first period of time divided by the third period of time described below is a whole number;
2. Providing a reagent pipetting section having a plurality of independent reagent pipetting stations each operating on a cycle of a second period of time, where the quotient of the second period of time divided by the third period of time is a whole number, and the number of the independent reagent pipetting stations being equal to the whole number;
3. Staggering apart respective cycles of the independent reagent pipetting stations by the third time period, such that at least one of the multiple independent pipetting stations is available for working with the sample aliquoting section at each operating cycle of the first period of time; and
4. Providing an incubate-wash-read section operating on a cycle of a third period of time, to match the desired throughput of the instrument system.

Such an arrangement has been found to provide a number of advantages. As explained in greater detail below, the new method and system for automated immunochemistry analysis of the present invention are capable of having a higher throughput, and also capable of being connected to other analyzers through a common sample handling unit, and further being capable of providing multiple pipetting modules that can work independently to ensure uninterrupted analysis, even when one of the modules malfunctions. In addition, the new method and system for automated immunochemistry analysis of the present invention are capable of performing reflex testing with a large capacity chilled sample storage area. Furthermore, the new method and system for automated immunochemistry analysis of the present invention have incorporated several novel and unique devices, including a sample presentation unit, a vessel loading apparatus that is capable of handling a bulk quantity of vessels, and a pick-and-place transporting device, which transports the vessels among various working areas of the system without dragging or jarring the vessels or splashing the contents of the vessels.

The system of the present invention may be used in connection with other chemical analyzer, such as, but not limited to, chemistry and hematology diagnostic instrumentation. Examples of such an instrumentation include Beckman Coulter Inc.'s Synchron Clinical Systems (Beckman Coulter Inc. Calif.).

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

The present invention is directed to a new method and system for an automated immunochemistry analysis. The system of the present invention includes the provision of an automated immunochemistry analyzer, and the method of the present invention includes the provision of the procedures of an automated immunochemistry analysis.

Figure 1:
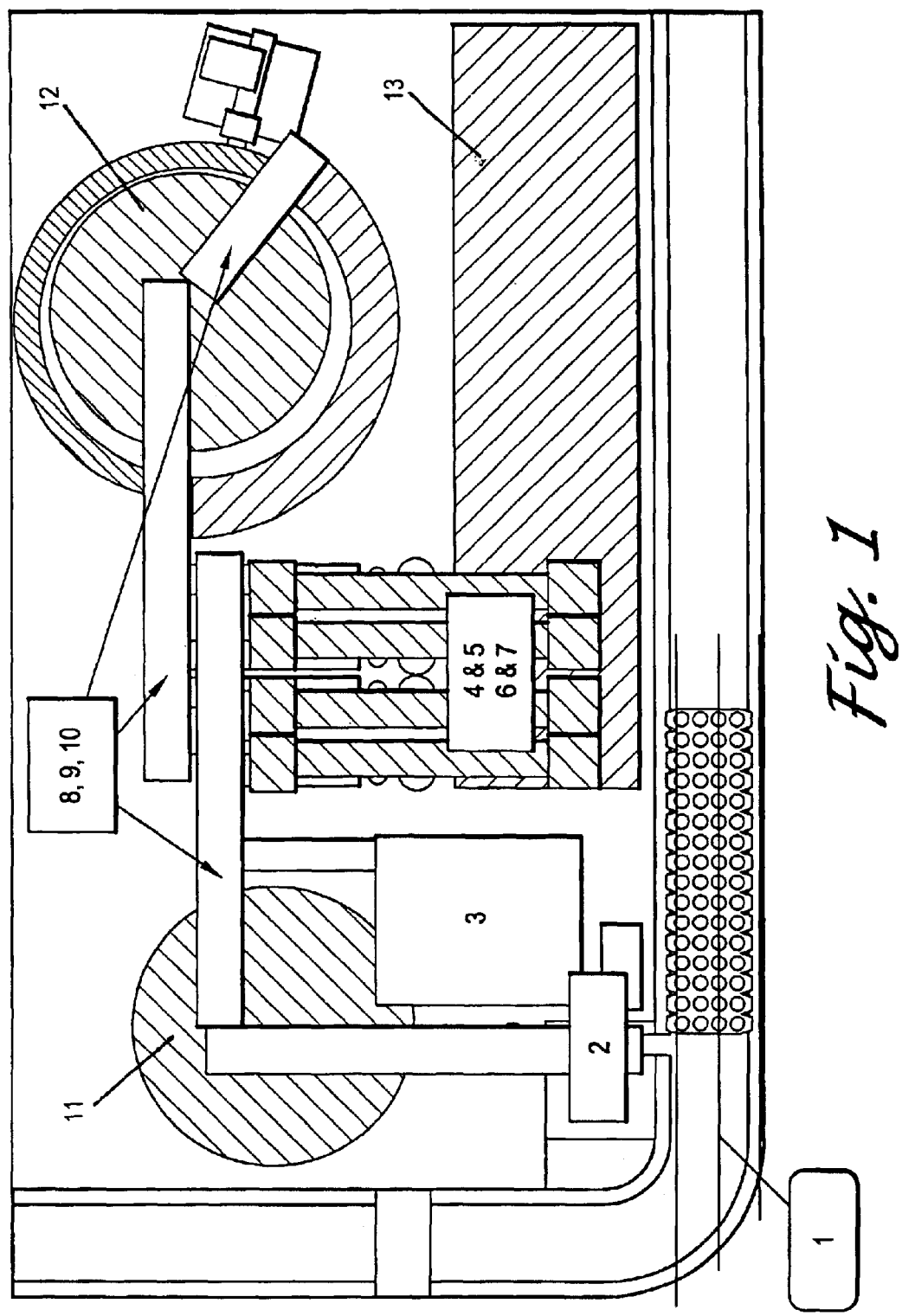
FIG. 1 is an illustrative block diagram showing the basic structural and functional modules of the automated immunochemistry analyzer of the present invention.

Referring to FIG. 1, there is shown an illustrative block diagram demonstrating the basic structural and functional modules of the automated immunochemistry analyzer of the present invention.

The basic structural and functional modules of the automated immunochemistry analyzer of the present invention includes a sample presentation unit 1, a main sample pipetting station 2, a bulk vessel feeder 3, first dual reagent pipetting stations 4 and 5, second dual reagent pipetting stations 6 and 7, a first pick-and-place gripper 8, a second pick-and-place gripper 9 and a third pick-and-place gripper 10, a chilled sample storage 11, an incubator/wash/read station 12, and a reagent storage 13.

The sample presentation unit 1 is used to transport the entire required test sample to and from the main sample pipettor 2. A detailed description of the configurations and functions of the sample presentation unit 1 is provided in the Assignee's co-pending patent application for "Sample Presentation Unit", patent application Ser. No. 09/848,450, filed May 3, 2001, and is incorporated herein by reference.

The main sample pipettor 2 is used to aspirate samples out of the sample tubes and dispense them into sample vessels supplied by the bulk vessel feeder 3. A detailed description of the configurations and functions of the bulk vessel feeder 3 is provided in the Assignee's co-pending patent application for "Bulk Vessel Feeder", patent application Ser. No. 09/777,750 filed Feb. 6, 2001, and is incorporated herein by reference.

The four reagent pipetting stations 4, 5, 6, and 7 are used to mix a sample with reagents for subsequent assay. The four reagent pipetting stations 4, 5, 6, and 7 are arranged as two dual pipetting stations and are independent to each other, each having its own fluid pumps and valves, wash towers, reaction vessel carriages, and pipettor. The individual structures and functions of each of these reagent pipetting stations 4, 5, 6, and 7 conform to existing arrangements used in the Access Instruments (Beckman Coulter, Inc., Calif.), which are known to those of ordinary skill in the art, and therefore will not be described in detail here.

The three vessel pick-and-place grippers 8, 9, and 10 are used to transport sample and reaction vessels among the various modules of the analyzer. The first pick-and-place gripper 8 is used to transport reaction vessels between the bulk vessel feeder 3 or the chilled sample storage 11 and the reagent pipetting stations 4, 5, 6, and 7. The second pick-and-place gripper 9 is used to transport reaction vessels between the reagent pipetting stations 4, 5, 6, and 7 and the incubator of the incubator/wash/read station 12. The third pick-and-place gripper 10 is used to transport reaction vessels between the incubator and the wash wheel of the incubator/wash/read station 12. A detailed description of the configurations and functions of the vessel pick-and-place grippers 8, 9, and 10 is provided in the Assignee's co-pending patent application for "Method and System or Picking and Placing Reaction Vessels", patent application Ser. No. 09/771,471, filed Jan. 26, 2001, and is incorporated herein by reference.

The chilled sample storage 11 is used for storing the samples contained in the reaction vessels at a low temperature for a certain period of time, e.g., up to three (3) hours, so that the samples may be used for reflex testing. When a test is requested on a patient sample, the test outcome may drive a request for additional testing. This automatic request for additional tests is reflex testing. The time delay from the first aspiration to knowing if another test will be started can range to as long as 45 minutes or more. To hold a sample tube for such a period of time prevents the sample from being used in other places. If the tube is passed to other instruments, it may be difficult for a laboratory technician to find the tube and reload it on the instrument requesting the reflex test. To allow a single quick sample draw on sample tubes that might require reflex testing, a single aspiration (aliquot) can be taken with sufficient test material for the possible reflex test(s). However, to insure that the test materials do not evaporate or deteriorate, the aliquot needs to be refrigerated on board the analyzer.

Figure 3:
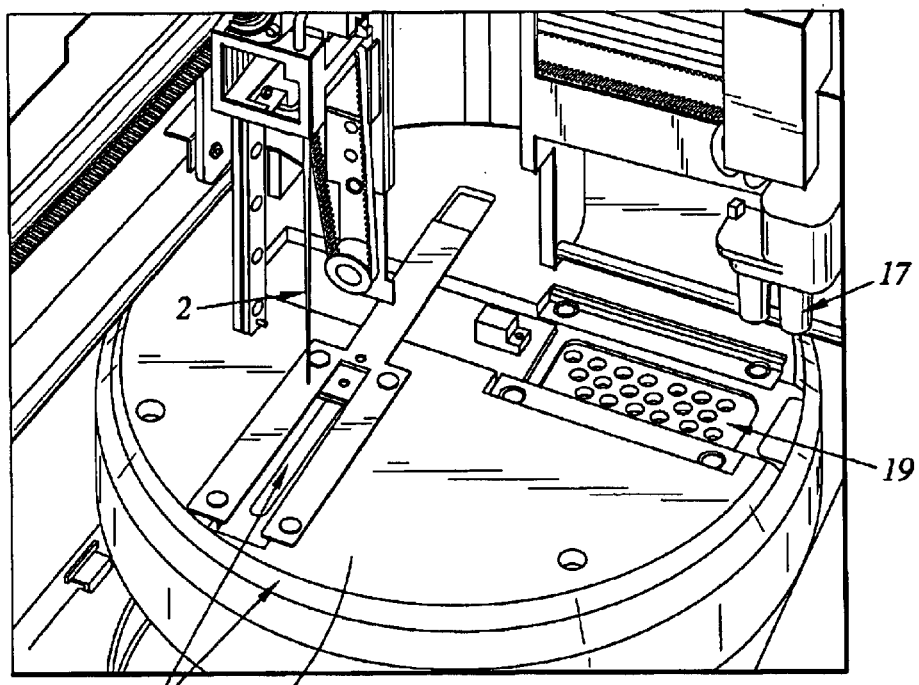
FIG. 3 is a perspective view showing the arrangement of the main sample pipetting station and the chilled sample storage of the automated immunochemistry analyzer of the present invention.

Referring to FIG. 3, there is shown the arrangement of the main sample pipetting station 2 and the chilled sample storage 11 of the automated immunochemistry analyzer of the present invention. The pipettor of the main sample pipetting station 2 first aspirates samples from sample tubes, and then moves into a position above the chilled sample storage 11. Meanwhile, the chilled sample storage 11 first receives an empty sample vessel from the bulk vessel feeder 3 by the pick and place gripper 8, and then moves the empty sample vessel under the pipettor of the main sample pipetting station 2. The aspirated sample is then dispensed into the chilled sample vessel. Insulation and doors 18 are provided to control the environment in the chilled sample storage 11. The chilled sample storage 11 is a precision controlled refrigerator with multiple storage locations 19 capable of receiving and transferring sample vessels for or filled with sample material.

Figure 4:
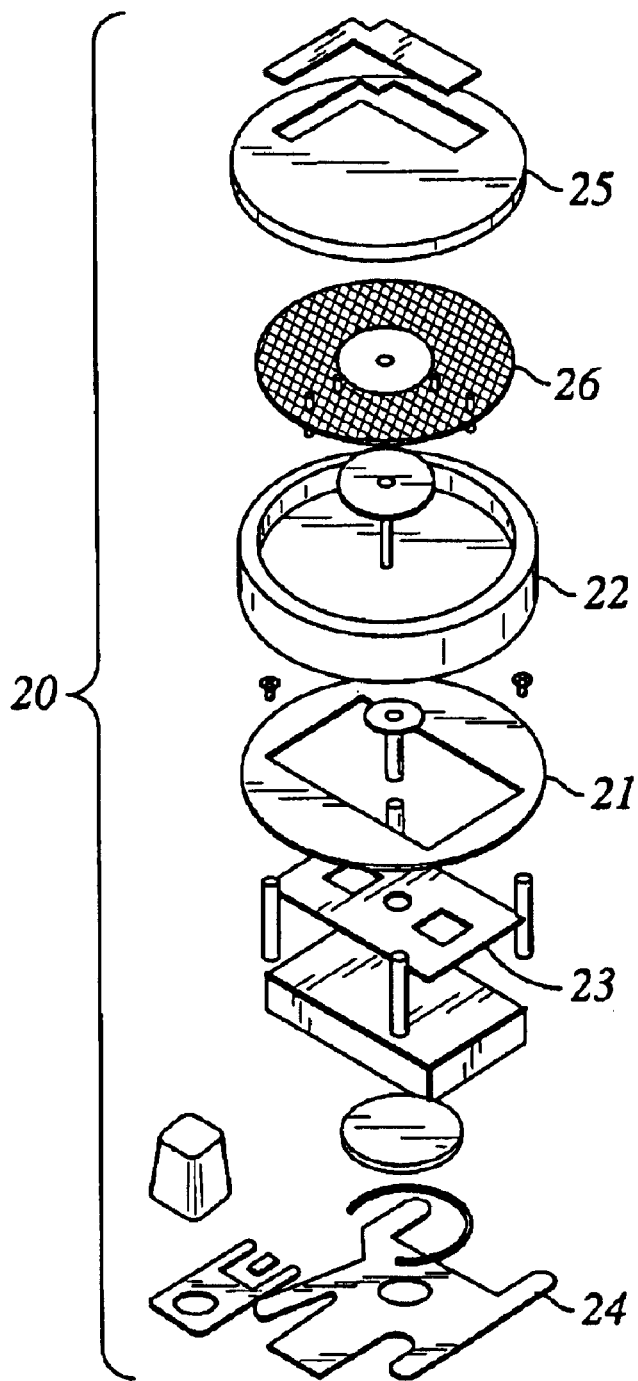
FIG. 4 is an exploded perspective view showing the arrangement of the sample chiller assembly of the automated immunochemistry analyzer of the present invention.

Referring to FIG. 4, there is shown an arrangement of the sample chiller assembly 20 of the chilled sample storage 11 of the automated immunochemistry analyzer of the present invention. The construction of the assembly 20 utilizes Peltier coolers 21 connected to a cold plate 22 and a heatsink 23. Heat is removed by blowing air over the heatsink 23. The unit is mounted on a base 24 and insulated with covers and doors 25. Reaction vessels containing samples are stored within the cooled area on a closed spaced storage plate 26 and kept in the cool environment until needed.

The incubator/wash/read station 12 is used for the incubating, washing, and reading steps of the assays. It may include one or more incubators, one or more washers, and one or more readers, such as a photomultiplier tube (PMT) detector. A detailed description of the configurations and functions of the incubator/wash/read station is provided in the Assignee's co-pending patent application entitled "Rotary Incubation of Immunoassay Vessels," filed concurrently with this application, the content of which in incorporated herein in its entirety by reference.

The reagent storage 13 is used for storing reagents used for the assays. It serves as the means for an operator to load reagent packs into the analyzer. It also serves as the means to store reagent packs in a refrigerated environment until requested for use, transfer the pack to the appropriate reagent pipetting station when requested for use, and return the pack to storage when pipetting is complete. It can also return a full or partially used pack to the operator when requested and automatically dispose of empty packs. The temperature in the reagent storage 13 is controlled by Peltier devices and monitored with a thermistor.

The reagent packs are loaded to the reagent storage 13 as follows: (a) an input tray cover is opened by the operator and the input tray is positioned, if necessary, to allow the operator to place reagent packs into the tray; (b) the input tray cover is closed and the input tray closes, bringing the reagent packs into the reagent storage 13; (c) as the input tray closes, each reagent pack position passes a bar code reader (BCR), where each of the four pack positions is read and identified; (d) a reagent pack gripper of a reagent pack transporting and sorting mechanism moves to get a pack from the input tray that was identified by the bar code reader; (e) the reagent pack gripper of the reagent pack transporting-and-sorting mechanism moves the reagent pack to either a storage location or a pipetting location (if needed), and drops the reagent pack off, and (f) the above steps (d) through (e) are repeated, until all reagent packs are removed from the input tray.

The reagent storage 13 includes a mechanism for transporting and sorting multiple reagent packs. A detailed description of the configuration and functions of such a mechanism for transporting and sorting multiple reagent packs is provided in the Assignee's co-pending patent application for "Method and System for Transporting and Storing Multiple Reagent Packs and Reagent Packs Used Therein", patent application Ser. No. 09/594,331, filed Jun. 15 2000, and is incorporated herein by reference. Other structures and functions of the reagent storage 13 conform to existing arrangements known to those of ordinary skill in the art, and therefore will not be described in detail here.

Figure 2:
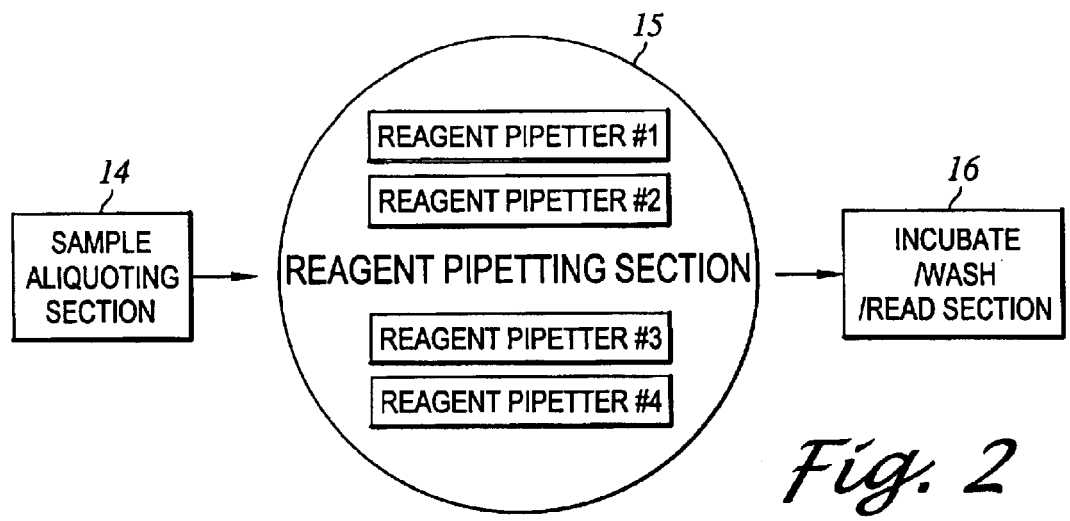
FIG. 2 is an illustrative flow chart diagram showing the basic operating procedures of the method of automated immunochemistry analysis of the present invention.

Referring to FIG. 2, there is shown an illustrative flow chart diagram showing the basic operating procedures of the method of automated immunochemistry analysis of the present invention.

The basic operating procedures of the automated immunochemistry analysis method of the present invention are carried out in three main sections of the automated immunochemistry analyzer: a sample aliquoting section 14, where the sample is aspirated out of a sample tube and dispensed into a sample vessel, a reagent pipetting section 15, where the sample is mixed with reagents, and an incubate/wash/read section 16, where the mixed sample is incubated, washed, and separated from particulates and read by the photo-multiplier tube (PMT) detector.

The sample aliquoting section 14 and the incubate/wash/read section 16 each only has one set of units and works on a nine (9)-second cycle. The reagent pipetting section 15 has four (4) independently working reagent pipetting stations, where each reagent pipetting station works on a thirty-six (36)-second cycle.

However, the four reagent pipetting stations are staggered nine (9) seconds apart. Therefore, the analyzer can accept one (1) test sample in every nine (9) seconds, i.e., the analyzer has an effective cycle of nine (9) seconds. Accordingly, the analyzer will have a fast throughput of four hundred (400) tests per hour. This is one of the main advantages of the analyzer of the present invention.

Another one of the advantages of having four reagent pipettors is that the redundancy ensures that the system will not be shut down if any one of the reagent pipettors malfunctions. When one of the reagent pipettors is not working properly, it can be shut down for inspection and repair, but the whole system can still keep processing assays (although at a lower throughput) because the other pipettors are still working.

Referring to FIGS. 1 and 2, the basic operating procedures of the sample aliquoting section 14, the reagent pipetting section 15, and the incubate/wash/read section 16 will be described below:

A. The Operating Cycle of the Sample Aliquoting Section 14

1. The operator loads a sample rack containing up to four (4) sample tubes on the sample presentation unit 1;
2. The rack is advanced into the main sample pipetting station 2 where the sample may be identified by a bar code reader (BCR) and presented to the main sample pipetting station 2;
3. At the same time, the bulk vessel feeder 3 presents the sample vessel necessary for the tests to the sample reaction vessel carriage, from where the first pick-and-place gripper 8 picks the reaction vessel up and stores it in the chilled sample storage 11 and/or in the reaction vessel carriage of any one of the available reagent pipetting stations 4, 5, 6, and 7; and 4. The main sample pipetting station 2 aspirates the amount of sample required and aliquots it into the sample vessel in the chilled sample storage 11, and afterwards, the probe is washed in its dedicated wash station.

The sample probe is washed to reduce sample carry-over to a level that will not adversely affect other samples.

B. The Operating Cycle of the Reagent Pipetting Section 15

1. The first pick-and-place gripper 8 picks up the sample vessel containing the aliquoted sample and moves it over to an available reagent pipetting station;

The following describes this process: (a) a requested sample vessel in the chilled sample storage 11 is positioned under an operating position of the first pick-and-place gripper 8; (b) a reaction vessel carriage of an available reagent pipetting station is positioned under another operating position of the first pick-and-place gripper 8; and (c) the first pick-and-place gripper 8 transfers the requested sample vessel from the chilled sample storage 11 to the reaction vessel carriage of the available reagent pipetting station.

2. At the same time the reagent storage 13 brings a reagent pack required to the same reagent pipetting station;

3. With the reagent pack and sample vessel in position, the reagent pipettor of that reagent pipetting station aspirates a required amount of sample from the sample reaction vessel and dispenses it into an assay reaction vessel and also retrieves a required amount of reagent from the reagent pack and dispenses it into the assay reaction vessel, and afterwards, the probe is washed in its dedicated wash station;

The following describes the process of sample aspiration: a) the reagent pipettor of the reagent pipetting station is positioned over the sample vessel; (b) an ultrasonic level sense circuit is used to detect the surface of the sample, and lowering of the pipettor is halted once the surface is found and the pipettor is just deep enough to draw the needed sample volume (therefore reducing carry-over); and (c) the sample is drawn up using the precision pump and valve, where an in-line pressure profile is collected by using a pressure sensor during the sample aspiration, which profile can be used to verify proper sample pickup. A detailed description of the configurations and functions of a precision pump and valve that are used herein are provided in the Assignee's co-pending patent applications for "Fluid-Moving Device with Integrated Valve", patent application Ser. No. 09/685,474, filed Oct. 10, 2000, now U.S. Pat. No. 6,520,755 and for "Fluid-Moving Device with a Clearance Seal", patent application Ser. No. 09/685,307, filed Oct. 10, 2000, respectively, and the content of which is incorporated herein by reference. Other structures and functions of the reagent pipetting stations are known to those of ordinary skill in the art, and therefore will not be described in detail here.

The following describes the process of reagent aspiration: (a) the reagent pipettor of the reagent pipetting station moves to the appropriate reagent well location of the reagent pack; (b) the reagent pipettor is lowered into the reagent pack well, and if this is a particle well, then an ultrasonic mix circuit is enabled (and the lock signal is checked to ensure proper operation) to mix the particles prior to aspiration; and (c) the reagent is drawn up using the precision pump and valve, where an in-line pressure profile is collected by using a pressure sensor during the reagent aspiration, which profile is used to verify proper reagent pickup.

The following describes the process of a sample or reagent delivery: (a) the reagent pipettor of the reagent pipetting station moves to the assay reaction vessel location in the reaction vessel carriage of the pipetting station; (b) the reagent pipettor is lowered into the assay reaction vessel, where the exact dispense height is calculated to have the sample or reagent just touch the probe after it has been dispensed (to ensure that there is no sample or reagent drop left on the tip of the probe); and (c) the sample or reagent is dispensed using the precision piston pump and valve, where an in-line pressure profile is collected by using a pressure sensor during the sample delivery, which profile is used to verify proper sample or reagent delivery.

The following describes the process of sample dilution: (a) the appropriate sample reaction vessel is retrieved for pipetting; (b) the dilution location in a reagent vessel carriage of an available reagent pipetting station is positioned under the operating position of the first pick-and-place gripper 8; (c) the bulk vessel feeder supplies two empty vessels (the reaction vessel and the dilution vessel); (d) the first pick-and-place gripper 8 transfers both vessels simultaneously to the reagent vessel carriage of the available reagent pipetting station; (e) the sample is aspirated and delivered to the dilution vessel along with an additional volume of buffer using the precision piston pump and valve, where the exact dispense height is calculated to have the diluted sample just touch the probe after it has been dispensed (to ensure that there is no sample drop left on the tip of the probe) or to go slightly deeper if mixing is requested (in such case, the ultrasonic mix circuit is enabled and the lock signal is checked to ensure proper operation); (f) a specific volume of this diluted sample is aspirated using the precision pump and valve, where an in-line pressure profile is collected by using a pressure sensor during the aspiration, which profile is used to verify proper diluted sample pickup; (g) the original sample vessel is returned to the chilled sample storage 11 if there is sample left or is disposed of if it is empty; and (h) the vessel containing the diluted sample now becomes the sample vessel for the subsequent assay being processed.

The following describes the process of sample and reagent addition: (a) the requested sample is retrieved from the chilled sample storage 11; (b) the bulk vessel feeder supplies an empty reaction vessel to the vessel supply carriage; (c) the vessel supply carriage is positioned under the operating position of the first pick-and-place gripper 8; (d) the reagent vessel carriage of an available reagent pipetting station is positioned under the other operating position of the first pick-and-place gripper 8; (e) the first pick-and-place gripper 8 transfers the empty reaction vessel to the reagent vessel carriage of the available reagent pipetting station; (f) the reagent vessel carriage is positioned for pipetting; (g) the requested reagent pack is also positioned for pipetting; (h) the reagent pipettor of the reagent pipetting station moves to a reagent wash tower, then down into the reagent wash tower, for washing the probe; (i) the sample is aspirated and delivered to the reaction vessel; (j) the reagent pipettor moves to the reagent wash tower, then down into the reagent wash tower, for washing the probe; (k) the reagent pipettor aspirates the appropriate amount of reagent and delivers it to the reaction vessel; (l) the above steps (j) and (k) are repeated until all of the reagents have been delivered to the reaction vessel; (m) if reaction vessel mixing is desired, the probe moves down slightly and the ultrasonic mix circuit is enabled and the lock signal is checked to ensure the proper operation; (n) the reagent vessel carriage is positioned under an operating position of the second pick-and-place gripper 9; (o) an empty position on a reaction vessel incubator wheel is positioned under another operating position of the second pick-and-place gripper 9; (p) the second pick-and-place gripper 9 transfers the reaction vessel into the incubator of the incubating/wash/read station 12; (q) in the case of two or three step assays, the second pick-and-place gripper 9 will bring the reaction vessel back to a pipetting location and additional reagents will be added, and then the vessel is transferred back to the incubator of the incubating/wash/read station 12 by the second pick-and-place gripper 9 for the second or third incubation.

The reagent probe is washed to reduce sample and reagent carry-over to a level that will not adversely affect other samples or reagent. The following describes this process: (a) the ultrasonic circuit is enabled to wash the reagent probe; (b) a vacuum pump evacuates the tower, while the tower's evacuation line pressure is monitored to ensure that the tower is draining properly; (c) the probe is flushed internally with buffer using the precision pump and precision valve and showered externally using the peristaltic pump; and (d) the buffer flow is stopped while the vacuum pump and ultrasonic circuit run slightly longer to ensure that the probe is dried.

4. The second pick-and-place gripper 9 picks up the assay reaction vessel containing the mixture of sample and reagent and moves it over to an incubator wheel of the incubator/wash/read station 12; and 5. The first pick-and-place gripper 8 picks up the sample reaction vessel containing the remaining aliquoted sample and returns it to the chilled sample storage 11 if reflex testing is required or else ejects it to a waste container.

The following describes this process: (a) a sample storage location in the chilled sample storage 11 is positioned under the operating position of the first pick-and-place gripper 8; (b) the reaction vessel carriage of the reagent pipetting station is positioned under the other operating position of the first pick-and-place gripper 8; and (c) the first pick-and-place gripper 8 transfers the sample reaction vessel from the reaction vessel carriage of the available reagent pipetting station to the chilled sample storage 11.

C. The Operating Cycle of the Incubate/Wash/Read Section 16

1. The assay vessel remains in the incubator wheel for a programmed time at a controlled temperature with heater elements and is monitored with a thermistor, and then picked up by the third pick-and-place gripper 10 for washing;

2. The wash/read ring has multiple aspirate stations and multiple dispense stations and the assay reaction vessel goes through several operations, including particle washing, substrate addition and incubation, etc., under a controlled temperature with heater elements and monitored with a thermistor.

3. The assay reaction vessel is read by the reader/detector, and thereafter is put back to the incubator by the third pick-and-place gripper 10, and thereafter picked up and disposed in the waste container by the second pick-and-place gripper 9.

The operations of the analyzer are supported by necessary fluid systems, electronic control hardware; and software, including various sensors and micro-controller(s), electrical power supply units, motors, and driving mechanisms, and mechanical structures, and the determination of suitable materials and structures are well within the skill in the art in view of the instant disclosure.

In addition, the analyzer can be connected to other analyzers through a common handling unit. Multiple analyzers can be set in a serial configuration for slow assay processing or in parallel configuration for fast assay processing, without changing the assay processing cycles.

In general, the automated immunochemistry analyzer of the present invention includes: (a) a first working section operating on a cycle of a first period of time and performing one of the at least two procedures; (b) a second working section operating on a cycle of a second period of time and performing another one of the at least two procedures; (c) the cycles of the first and second working sections adjusted such that the quotient of the first period of time divided by the second period of time is a whole number; and (d) the first working section having a multiplicity of independent working stations, each operating on the cycle of the first period of time, the number of the working stations being equal to the whole number, and the respective cycles of such stations being staggered apart by the second period of time, such that at least one of the working stations of the first working section is available for working with the second working section at each operating cycle of the second working section to match the desired throughput of the instrument system.

The method of the automated immunochemistry analysis of the present invention includes the following steps: (a) adjusting the respective cycle of at least one of the at least two procedures, such that one of the least two procedures has an operating cycle of a first period of time and another one of the at least two procedures has an operating cycle of a second period of time, and the quotient of the second period of time divided by the first period of time is a whole number; (b) providing a plurality of independent working stations for performing the other one of the at least two procedures, each working station operating on the cycle of the second period of time, such that the number of such stations equal to the whole number; and (c) staggering apart respective cycles of the independent working stations by the first period of time, such that at least one of the working stations is available for each operating cycle of the first period of time.

It is noted that in the above broad description of the apparatus and method of the present invention, the terms "first" and "second" used in describing the working sections and their respective cycle of time periods are merely used to distinguish two sequential procedures in a process but do not designate the priority of these procedures. For example, the first work section may be a sample aliquoting section and the second section may be a reagent pipetting section, in which case the reagent pipetting section performs its functions subsequent to those of the sample aliquoting section. Alternatively, while the second section may still be a reagent pipetting section, the first section may be an incubate and wash and read section, in which case the incubate and wash and read section performs its functions subsequent to those of the reagent pipetting section.

The method and system for automated immunochemistry analysis of the present invention has many novel and unique features and advantages. First, the method and system for automated immunochemistry analysis of the present invention are capable of having a higher throughput, e.g., 400 tests per hour. The method and system for automated immunochemistry analysis of the present invention are also capable of being connected to other analyzers through a common sample presentation unit. The method and system for automated immunochemistry analysis of the present invention are further capable of providing multiple pipetting modules that can work independently to ensure uninterrupted analysis, even when one of the modules malfunctions. Moreover, the method and system for automated immunochemistry analysis of the present invention are capable of performing reflex testing with a large capacity chilled sample storage area.

In addition, the method and system for automated immunochemistry analysis of the present invention have incorporated several novel and unique devices. These novel and unique devices include a sample presentation unit that is capable of being used with various analyzers, a vessel loading apparatus that is capable of handling a bulk quantity of vessels, and a pick-and-place transporting device, which transports the vessels among various working areas of the system without dragging or jarring the vessels or splashing the contents of the vessels.

The foregoing is meant to illustrate, but not to limit, the scope of the invention. Indeed, those of ordinary skill in the art can readily envision and produce further embodiments, based on the teachings herein, without undue experimentation.

It is to be understood that the form of the system depicted in FIGS. 1 through 4 has been chosen only for the purpose of describing a particular embodiment and function of the invention, and that the arrangement of the invention can be addressed in various ways and incorporated in other types of devices, all of which will be evident to those working in the art.

It is to be understood that the particular arrangement of the present invention may vary, depending on the chemical analyzer instrument it is incorporated or working together with, but that the determination of necessary variation is well within the skill in the art in view of the instant disclosure.

Suitable components that are commercially available would be known to those of ordinary skill in the art in view of this disclosure.

It is further understood that any comparable means of accomplishing this goal is within the scope of this invention.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. An apparatus for automated immunochemistry analysis having at least two procedures requiring different operating cycles, comprising:
   a. a first working section operating on a cycle of a first period of time and performing one of said at least two procedures, wherein said first working section is a reagent pipetting section;
   b. a second working section operating on a cycle of a second period of time and performing another one of said at least two procedures, wherein said second working section is a sample aliquoting section;
   c. said cycles of said first and second working sections adjusted such that the quotient of said first period of time divided by said second period of time is a whole number; and
   d. said first working section having a multiplicity of independent working stations, each operating on said cycle of said second period of time, the number of said stations being equal to said whole number, and the respective cycles of such stations being staggered apart by said second period of time, such that at least one of said working stations of said first working section is available for working with said second working section at each operating cycle of said second working section.

2. The apparatus as defined in claim 1, further comprising a third working section, wherein said third working section is an incubate and wash and read section.

3. An apparatus as defined in claim 1 wherein said operating cycle of said second working section is nine (9) seconds.

4. The apparatus as defined in claim 1, wherein said operating cycle of each said independent working station of said first working section is thirty-six (36) seconds.

5. The apparatus as defined in claim 4, wherein said first working section includes four (4) independent working stations in said reagent pipetting section.

6. The apparatus as defined in claim 5, wherein the respective operating cycles of said four (4) independent pipetting stations of said reagent pipetting section are staggered apart by nine (9) seconds.

7. An apparatus for automated immunochemistry analysis, comprising:
   a. a sample aliquoting section having an operating cycle of a first period, and including a main sample pipetting station for aliquoting a desired amount of sample from a sample vessel to a reaction vessel;
   b. a chilled storage for storing multiple reaction vessels containing the aliquoted sample
   c. a reagent pipetting section including a multiple independent pipetting stations each having an operating cycle of a second period of time;
   d. a reagent storage for storing multiple reagent packs, each containing at least one reagent; and
   e. said multiple independent pipetting stations each having a pipettor for aspirating a required amount of sample from said at least one of said reaction vessels containing an aliquoted sample and dispensing it into an assay vessel, and aspirating a required amount of reagent from said at least one of said reagent packs, containing at least one reagent and dispensing it into said assay vessel;
   f. an incubate and wash and read section having an operating cycle of a third period of time to match a desired throughput of said apparatus;
   g. the quotient of the second period of time divided by the third period of time is a whole number, the number of said multiple independent stations of said reagent pipetting section being equal to said whole number, and the respective cycles of such stations being staggered apart by said third period of time, such that at least one of said stations is available for each operating cycle of said incubate and wash and read section.

8. The apparatus as defined in claim 7 further comprising a sample presentation unit for loading and unloading of sample racks, each containing multiple sample vessels.

9. The apparatus as defined in claim 7 further comprising a bulk vessel feeder for supplying empty reaction vessels.

10. The apparatus as defined in claim 7, wherein said chilled storage further comprises means for positioning reaction vessels stored therein for storage or transportation.

11. The apparatus as defined in claim 7 further comprising a picking and placing means for transferring at least one reaction vessel containing aliquoted sample from said main pipetting station or said chilled storage to one of said multiple independent pipetting stations.

12. The apparatus as defined in claim 11, wherein said picking and placing means also transfers said at least one reaction vessel from said reagent pipetting section back to said chilled storage if there is still sample remaining and reflex testing is required.

13. The apparatus as defined in claim 11, wherein said picking and placing means also disposes said at least one reaction vessel from said reagent pipetting section to a waste container if there is no more sample remaining.

14. The apparatus as defined in claim 7, wherein said reagent storage further comprises a transporting and sorting means for presenting at least one reagent pack to one of said multiple independent pipetting stations.

15. The apparatus as defined in claim 7 further comprising a picking and placing means for transferring an assay vessel from said reagent pipetting section to said incubate and wash and read section.

16. The apparatus as defined in claim 15, where said second picking and placing means also transfers said assay vessel from said incubate and wash and read section back to said reagent pipetting section if multiple step assay is required.

17. The apparatus as defined in claim 15, wherein said picking and placing means also disposes said assay vessel from said incubate and wash and read section to a waste container if there is no more assay need to be performed.

18. The apparatus as defined in claim 7, wherein said incubate and wash and read section further comprises at least one incubating station.

19. The apparatus as defined in claim 18, wherein said incubate and wash and read section further comprises at least one wash and read station.

20. The apparatus as defined in claim 19 further comprising a picking and placing means for transferring an assay vessel from said at least one incubator station to at least one said wash and read station.

21. The apparatus as defined in claim 7, wherein each said independent pipetting station of said reagent pipetting section is also capable of diluting said aliquoted sample.

22. The apparatus as defined in claim 7, wherein said operating cycle of said incubate and wash and read section is nine (9) seconds.

23. The apparatus as defined in claim 22, wherein said operating cycle of each one of said multiple independent pipetting stations of said reagent pipetting section is thirty-six (36) seconds.

24. The apparatus as defined in claim 23, wherein said reagent pipetting section includes four (4) independent pipetting stations.

25. The apparatus as defined in claim 24, wherein the respective operating cycles of said four (4) independent pipetting stations of said reagent pipetting section are staggered apart by nine (9) seconds.

26. The apparatus as defined in claim 22, where said sample aliquoting section also has an operating cycle of nine (9) seconds.

27. An apparatus for automated immunochemistry or chemistry analysis, comprising:
  a. a sample presentation unit for loading and unloading of sample racks, each containing multiple sample vessels;
  b. a bulk vessel feeder for supplying empty reaction vessels
  c. a sample aliquoting section having an operating cycle of a first period of time, and including a main sample pipetting station for aliquoting a desired amount of sample from a sample vessel to at least one of said empty reaction vessels;
  d. a chilled storage for storing multiple reaction vessels containing the aliquoted sample;
  e. a reagent pipetting section including multiple independent pipetting stations, each having an operating cycle of a second period of time,
  f. a first picking and placing means for transferring said at least one of said reaction vessels containing the aliquoted sample from said main pipetting station or said chilled storage to one of said multiple independent pipetting stations;
  g. a reagent storage for storing multiple reagent packs, each containing at least one reagent and including a transporting and sorting means for presenting at least one of said reagent packs to said one of said multiple independent pipetting stations;
  h. said multiple independent pipetting stations each having a pipettor for aspirating a required amount of sample from said at least one of said reaction vessels containing aliquoted sample and dispensing it into an assay vessel, and aspirating a required amount of reagent from said at least one of said reagent packs containing at least on reagent and dispensing it into said assay vessel;
  i. an incubate and wash and read section having a third operating cycle to match the throughput of said apparatus, and including an incubator wheel and a wash and read ring;
  j. the quotient of the second period of time divided by the third period of time is a whole number, the number of said multiple independent pipetting stations of said reagent pipetting section being equal to said whole number, and the respective cycles of such stations being staggered apart by said third period of time, such that at least one of said multiple independent pipetting station is available for each operating cycle of said incubate and wash and read section;
  k. a second picking and placing means for transferring said assay vessel from said reagent pipetting section to said incubator or wheel for incubation; and
  l. a third picking and placing means for transferring said assay vessel from said incubator wheel to said wash and read ring for washing and reading by a detection device.

28. The apparatus as defined in claim 27, wherein said operating cycle of said incubate and wash and read section is nine (9) seconds.

29. The apparatus as defined in claim 28, wherein said operating cycle of each said independent pipetting station of said reagent pipetting section is thirty-six (36) seconds.

30. The apparatus as defined in claim 29, wherein said reagent pipetting section includes four (4) independent pipetting stations.

31. The apparatus as defined in claim 30, wherein the respective operating cycles of said four (4) independent pipetting stations of said reagent pipetting section are staggered apart by nine (9) sections.

32. The apparatus as defined in claim 28, wherein said sample aliquoting section also has an operating cycle of nine (9) seconds.

33. The apparatus as defined in claim 27, wherein said chilled storage further comprises means for positioning reaction vessels stored therein for storage or transportation.

34. The apparatus as defined in claim 27, wherein each said independent pipetting station of said reagent pipetting section is also capable of diluting said aliquoted sample.

35. The apparatus as defined in claim 27, wherein said first picking and placing means also transfers said reaction vessel containing aliquoted sample from said reagent pipetting section back to said chilled storage if there is still sample remaining and reflex testing is required.

36. The apparatus as defined in claim 27, wherein said second picking and placing means also transfers said assay vessel from said incubate and wash and read section back to said reagent pipetting section if multiple step assay is required.

37. A method of automated immunochemistry or chemistry analysis having at least two procedures requiring different operating cycles, comprising the steps of:
 a. adjusting said respective cycle of at least one of said at least two procedures, such that one of said at least two procedures has an operating cycle of a first period of time and another one of said at least two procedures has an operating cycle of a second period of time, and the quotient of said first period of time divided by said second period of time is a whole number, wherein said one of said at least two procedures is reagent pipetting, and said other one of said at least two procedures is sample aliquoting;
 b. providing a plurality of independent working stations for performing said one of said at least two procedures, each working station operating on said cycle of said second period of time, such that the number of such stations is equal to said whole number; and
 c. staggering apart respective cycles of said independent working stations by said second period of time, such that at least one of a said working stations is available for each operating cycle of said second period of time.

38. The method as defined in claim 37 further comprising the step of providing at least one working station operating on said cycle of said second period of time for performing said other one of said at least two procedures.

39. The method as defined in claim 37, further comprising a third procedure, wherein said third procedure is incubating and washing and reading.

40. The method as defined in claim 37 wherein said operating cycle of said second period of time of said other one of said at least two procedures is nine (9) seconds.

41. The method as defined in claim 37 wherein said operating cycle of said first period of time of said one of said at least two procedures is thirty-six (36) seconds.

42. The method as defined in claim 41, wherein said number of said independent working stations for performing said one of said at least two procedures is four (4).

43. The method as defined in claim 42, wherein the respective operating cycles of said four (4) independent working stations are staggered apart by nine (9) seconds.

44. A method of automated immunochemistry or chemistry analysis, comprising the steps of:
 a. providing a sample aliquoting section operating on a cycle of a first period of time;
 b. providing a reagent pipetting section having a plurality of independent reagent pipetting stations each operating on a cycle of a second period of time, wherein each pipetting station can dispense a liquid;
 c. providing an incubate and wash and read section operating on a cycle of a third period of time to match a desired throughput of said apparatus;
 d. the quotient of said second period of time divided by a third period of time is a whole number, and the number of the independent reagent pipetting stations of said reagent pipetting section being equal to the whole number;
 e. staggering apart respective cycles of said independent reagent pipetting stations by said third period of time, such that at least one of said multiple independent pipetting stations is available for working with said incubate and wash and read section at each operating cycle of said third period of time.

45. The method as defined in claim 44 wherein said operating cycle of said sample aliquoting section is nine (9) seconds.

46. The method as defined in claim 45 wherein said operating cycle of each said independent reagent pipetting station of said reagent pipetting; section is thirty-six (36) seconds.

47. The method as defined in claim 46, wherein said number of said independent reagent pipetting stations is four (4).

48. The method as defined in claim 47, wherein the respective operating cycles of said four (4) independent pipetting stations are staggered apart by nine (9) seconds.

* * * * *